US008652042B2

(12) United States Patent
Mattoli et al.

(10) Patent No.: US 8,652,042 B2
(45) Date of Patent: Feb. 18, 2014

(54) SENSING MOISTURE LEVEL OF HUMAN SKIN (75) Inventors: Virgilio Mattoli, Pisa (IT); Francesco Greco, Massa e Cozzile (Pistoia) (IT); Lucia Beccai, Livorno (IT); Paolo Dario, Livorno (IT)

(73) Assignee: Fondazione Istituto Italiano di Technologia, Genoa (IT)

( * ) Notice: Subject to any disclaimer, the term of this patent is extended or adjusted under 35 U.S.C. 154(b) by 0 days.

(21) Appl. No.: 13/637,347

(22) PCT Filed: Mar. 28, 2011

(86) PCT No.: PCT/IB2011/051299
§ 371 (c)(1),
(2), (4) Date: Nov. 28, 2012

(87) PCT Pub. No.: WO2011/121518
PCT Pub. Date: Oct. 6, 2011

(65) Prior Publication Data
US 2013/0066170 A1    Mar. 14, 2013

(30) Foreign Application Priority Data
Mar. 29, 2010   (IT) .......................... FI2010A000053

(51) Int. Cl.
*A61B 5/053*        (2006.01)
(52) U.S. Cl.
USPC .......................................... 600/306; 600/547
(58) Field of Classification Search
USPC .......... 600/306, 547; 324/634, 640, 664, 689, 324/694
See application file for complete search history.

(56) References Cited

U.S. PATENT DOCUMENTS

| 7,402,135 | B2 * | 7/2008 | Leveque et al. ............... 600/306 |
| 2002/0137992 | A1 | 9/2002 | Lahtinen |
| 2005/0103091 | A1 * | 5/2005 | Stockinger ..................... 73/1.01 |
| 2006/0248946 | A1 | 11/2006 | Howell et al. |
| 2008/0306471 | A1 | 12/2008 | Altshuler et al. |
| 2009/0009193 | A1 * | 1/2009 | Hsiung et al. ................. 324/664 |
| 2009/0312615 | A1 | 12/2009 | Caduff et al. |

FOREIGN PATENT DOCUMENTS

WO    2007/026339    3/2007

OTHER PUBLICATIONS

Han, J.Y. Low-Cost Multi-touch Sensing Through Frustrated Total Internal Reflection. 2005. Proc. UIST '05, ACM Press, pp. 115-118.*

(Continued)

*Primary Examiner* — Navin Natnithithadha
*Assistant Examiner* — Meredith Weare
(74) *Attorney, Agent, or Firm* — Steinfl & Bruno LLP (57) ABSTRACT A human skin moisture measuring device having an interdigitated resistive sensor formed on a plate-like transparent support is described, with a face designed to be placed into contact with the skin to be subjected to the moisture degree measurement. The device further comprises image sensing means turned towards the opposite face of the support and a lighting device arranged sideways relative to the support to direct the light radiation in the support at a prefixed angle. Means for processing the signal coming from the interdigitated resistive sensor and from the image sensing means give as output a value of the measured moisture degree that is normalized with respect to the actual surface of contact between skin and sensor.

10 Claims, 5 Drawing Sheets

(56) References Cited

OTHER PUBLICATIONS

PCT International Search Report mailed May 24, 2011 for PCT/IB2011/051299 filed on Mar. 28, 2011 in the name of Scuola Superiore Di Studi Universitari E Di Perfezionamento Sant'Anna and Fondazione Istituto Italiano Di Tecnologia.
PCT Written Opinion mailed May 24, 2011 for PCT/IB2011/051299 filed on Mar. 28, 2011 in the name of Scuola Superiore Di Studi Universitari E Di Perfezionamento Sant'Anna and Fondazione Istituto Italiano Di Tecnologia.
Chen, Z., et al., Humidity Sensors: A Review of Materials and Mechanisms, Sensors Letters 2005, 3: 274-295.
Hanreich, G., et al., A new bonding technique for human skin humidity sensors, Sensors & Actuators A 2001, 92: 364-369.
Valentin B., et al., A Novel Transepidermal Water Loss Sensor, IEEE Sensors Journal 2006, 6: 1022-1026.

\* cited by examiner

SENSING MOISTURE LEVEL OF HUMAN SKIN

CROSS REFERENCE TO RELATED APPLICATIONS

The present application is the US national stage entry of International Application PCT/IB2011/051299 filed on Mar. 28, 2011, which in turn claims priority to Italian Application FI2010A000053, filed on Mar. 29, 2010.

FIELD OF THE INVENTION

The invention generally refers to the field of detecting and measuring moisture in a substrate and more in particular relates to a human skin moisture measuring device. The invention relates also to a method for carrying out the moisture measure.

PRIOR ART

Detection of the human skin water content, in particular the one contained in the horny layer (*Stratum Corneum*) of the epidermis, is a very important factor for cure thereof. As known, the horny layer is the outermost layer of the epidermis and consists of a superimposition of about 20 cell layers to form a thin membrane which covers the entire human body and constitutes the interface thereof with the surrounding atmosphere.

The diagnostic importance of the water content in the horny layer of the epidermis is well known. The knowledge of this parameter is useful for monitoring the health of the skin both from a medical point of view and from a dermocosmetic point of view. Actually skin hydration is a sign of the normal biological activity thereof, resulting in the continuous and normal flow of liquids from within the organism towards the surrounding environment. On the contrary, low levels of hydration of the horny layer are used as useful diagnostic signals in pathologies such as atopic dermatitis.

From a cosmetic point of view or more generally from a personal wellness point of view, the "healthy" aspect of the skin—directly related to hydration thereof—is one of the factors known and perceived as fundamental for defining the beauty, for example, of a face; in the case of the skin of the scalp, the poor hydration leads to dandruffs with ensuing flare, irritation, itchiness, desquamations.

The barrier properties of the skin are also improved by good hydration of the skin, with ensuing lower loss of moisture. Thus, besides the aspect of the skin the water content in the horny layer also influences the absorption of drugs and other substances through the skin.

Given the evident scientific/medical and commercial importance of the state of skin hydration, the development of electronic or optoelectronic devices for detecting the water content in the skin is subject of an extensive scientific literature: see for example: Chen, Z. et al., *Humidity sensors: A review of materials and mechanisms*, Sensor Letters, 2005. 3(4): pg. 274-295. The development of sensors for this application with innovative solutions follows the more general rapid development of the bioengineering and biomedical applications and the micro-manufacturing processes; actually, they allow providing miniaturized or portable sensors capable of measuring various physiological parameters in a qualitative, efficient and repeatable manner.

Various techniques were used over the last years for measuring the degree of human skin moisture and some of them were also exploited in some instruments available in the market over the years and used in dermatological and cosmetic research as well as in diagnosis, such as for example the instrument known by the name Nova DPM 9003® manufactured by Nova Technology Corp. based on conductance measurements, or instruments based on capacitive measurements, such as the class of Corneometer® instruments manufactured by the German company CK Electronics GmbH.

As a general attempt of classifying human skin moisture sensors they can be classified according to the type of measurement used. Actually, there are:
- "resistive" sensors, i.e. sensors employing electrical resistivity measurement.
- "capacitive" sensors, i.e. sensors employing electrical capacity measurements.
- "optical" sensors, i.e. sensors employing light (not only in the visible radiation range, but also in the ultraviolet or infrared range) for optical, photonic, photometric measurements.

On the subject, see for example patent applications US2006248946, WO2007026339 and US2002137992.

These methods commonly provide for a similar measurement strategy: the application of a sensitive "head" into contact with the skin. The degree of moisture of the latter determines a variation—in the electrical properties—of an electrical measurement circuit comprised in the head (or a variation in the overall refractive index, in case of optical measurements).

Alongside this, there is the further strategy based on the so-called transepidermal water loss (TEWL)—a physical quantity expressed in grams of water per square meter and per hour. According to this method the detection system is mounted in a measurement chamber which is applied to the skin surface. The water vapour emitted by the skin fills the measurement chamber causing an increase of the relative moisture. The measurement of the increasing vapour rate which condensates on the relatively cooler surface of the sensor allows evaluating skin hydration (see: B. Valentin et al., *A novel transepidermal water loss sensor*, IEEE Sens. J. 6 (2006) 1022-1026). This second strategy is however not commonly used, also due to the inevitable complications and due to the overall dimensions of the device, thus hindering use in portable and/or miniaturized devices.

The contact between the sensitive element and the skin is thus one of the fundamental factors in the process of measuring the degree of skin moisture. Such aspect reveals considerable technological and manufacturing drawbacks and it is thus subject of studies (G. Hanreich et al., *A new bonding technique for human skin humidity sensors*, Sens. Actuators A: Phys. 92 (2001) 364-369). Various solutions adapted to improve the adhesion of the electrodes to the rough surface of the skin were proposed. Actually, from one point of view it is necessary that the sensitive surface be as smooth as possible, so as to eliminate inaccuracies in the measurements due to the positioning of the dermic surface in areas of the sensor characterized by different topography, at the same time the horny layer is inherently characterized by an extremely variable and discontinuous topography. It is made of depressions and crests (epidermic crests) whose curvature and length varies among individuals and among the different areas of the body (hands, neck, forehead, scalp, etc.).

In order to overcome this drawback, in WO2007026339 there is for example described the use of extensible/telescopic electrodes capable of adapting to the topography of the horny layer. The use of extremely smooth sensitive polyimide surfaces and a configuration wherein the sensor is kept at position and pressed with controlled pressure on the skin by a spring are described in US2009009193. In particular, in this case there is described a method for manufacturing a sensor for detecting the degree of human skin moisture, just like the environmental one, based on a series of interdigitated electrodes on PCB (interdigitated capacitor) and a thin polyimide layer superimposed thereon by hot moulding serving as a sensitive layer, modifying the capacity of the capacitor connected to an impedance measuring device. The moisture measurement is of the capacitive type and is based on the variation of the electrical properties in the polyimide film as a function of the moisture.

Additionally, given the natural flexibility and elasticity of the skin, the extension of the area at contact with the sensitive surface of the sensor and the skin further depends on the force by which the sensor is pressed against the skin, or vice versa; the pressure by which the final user places the finger thereof on the sensor to measure the skin moisture degree thereof introduces other inaccuracy and irreproducibility elements in the measurements.

Usually, the commercial systems use a fixed area surface, which must be entirely at contact with the skin to be measured, but this solution may not be satisfactory, in that it is not always possible to ensure that this condition is met or even only verify the divergence therefrom in any measurement carried out. Furthermore, the fact of not being able to access the contact area in any manner whatsoever excludes a series of applications that could be of considerable scientific interest (and thus even industrial interest), such as, for example, the study of the dynamics and perception of the touch in correlation to the degree of skin moisture.

Thus, lastly, one of the most important problems that arise in the known systems for measuring the degree of human skin moisture is given by the fact that the accuracy of such measurement in general (both in the case of resistive and capacitive transduction) depends on the actual surface of contact between the skin and the transducer.

Thus, the general object of the present invention is that of overcoming the previously mentioned drawbacks of the devices for measuring the degree of human skin moisture according to the prior art.

In particular the present invention aims at providing a human skin moisture measuring device capable of accurately performing such measurement regardless of the degree of contact between skin and transducer.

Another particular object of the present invention is to provide a moisture measurement device of the abovementioned type capable of providing a normalised measurement of the skin moisture.

A further object of the present invention is to provide a moisture measurement device of the abovementioned type capable of allowing visual access to the skin-transducer contact surface during the measurement.

SUMMARY OF THE INVENTION

These objects are attained through the method and device for measuring skin moisture according to the invention whose essential characteristics are outlined in claims 1 and 6. Further important characteristics of the moisture measurement device according to the invention are indicated in the dependent claims.

According to an important aspect of the invention, the accurate measurement of the degree of skin moisture is obtained through resistive transduction using an entirely transparent sensor, through which it is possible to see the contact area and accurately measure the area thereof for normalizing the signal and, if required, acquire the image thereof for other purposes, such as for example tactile perception studies.

BRIEF DESCRIPTION OF THE DRAWINGS

Characteristics and advantages of the human skin moisture measuring device shall be apparent from the following description of an embodiment thereof provided solely by way of non-limiting example with reference to the attached drawings wherein.

DETAILED DESCRIPTION OF THE INVENTION

Figure 1:
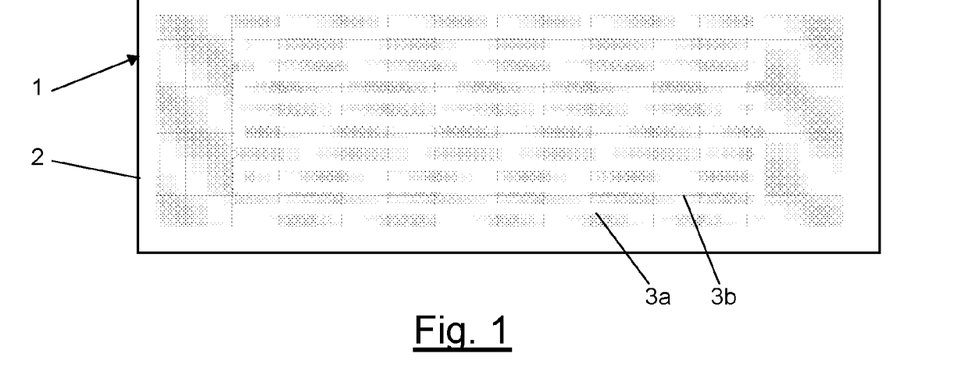
FIG. 1 illustrates a possible layout of a moisture sensor employed in the system according to the present invention.

With reference to FIG. 1, it has been generally indicated at 1 a transparent moisture sensor constituted by a substrate 2 made of glass (or quartz or any other transparent material suitable to serve as a substrate) on which there are created two interdigitated electrodes 3a and 3b made of transparent and conductive material, such as for example ITO (Indium Tin Oxide). The shape and the dimensions of the electrodes may vary as a function of the accuracy and the spatial resolution intended to be obtained in the measurement. This allows obtaining an entirely transparent resistance sensor, and thus a skin moisture sensor. Various construction processes, being part of the known microsystems technologies, such as for example optical lithography, can be used to obtain such transparent electrodes.

Figure 2:
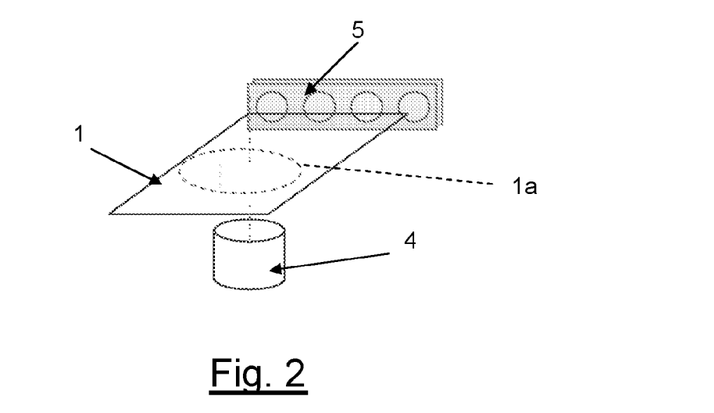
FIG. 2 schematically illustrates the device for measuring the degree of skin moisture according to the invention.

As shown in FIG. 2, the moisture sensor 1 is associated to an image sensor 4 and a lighting device 5. The image sensor 4 is for example constituted by a camera, a CCD or a C-MOS arranged at a face on the moisture sensor 1, facing the contact area. In particular, the moisture sensor 1 is interposed between the image sensor 4 and the surface of the skin to be subjected to the moisture measurement with detection axis substantially perpendicular to the contact surface of the moisture sensor schematically indicated with 1a in FIG. 2. The lighting device 5 is made up of one or more light sources (LED or any other) which direct the light radiation into the sensor 1 through the side flank or thickness 1b of the plate that constitutes it. The flat plate forming the moisture sensor 1 is thus substantially coplanar to the lighting device.

The lighting device 5 is used to accurately indicate the part of the skin actually at contact with the moisture sensor and to allow an accurate measurement of the contact area through the image sensor 4.

Figure 3:
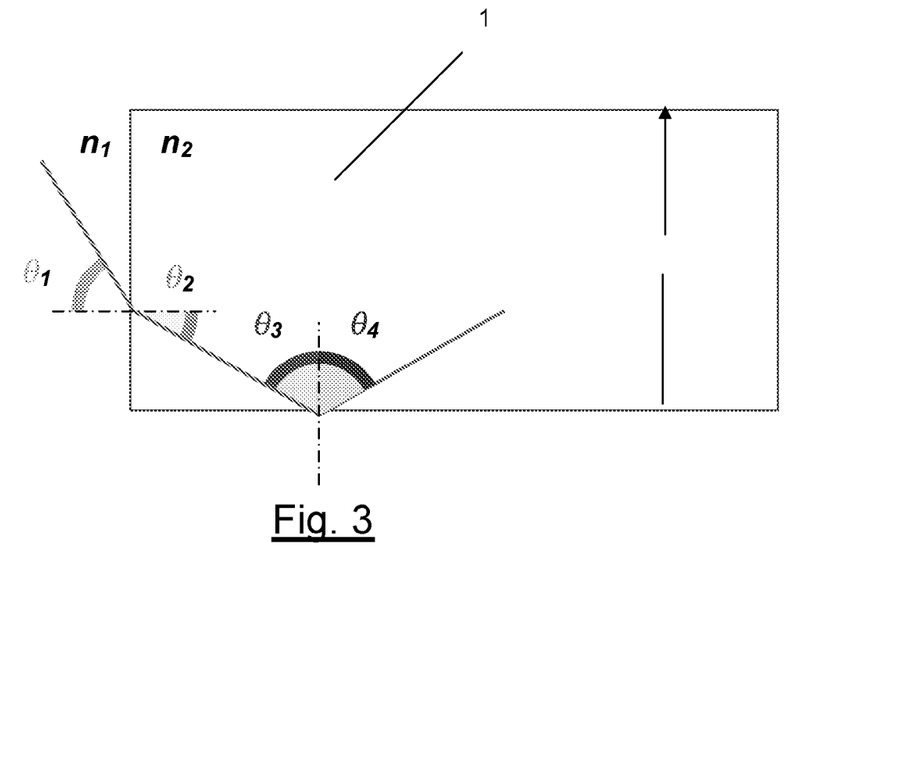
FIG. 3 is a simplified diagram of the total reflection of the light within the sensor of FIG. 1.
Figure 4:
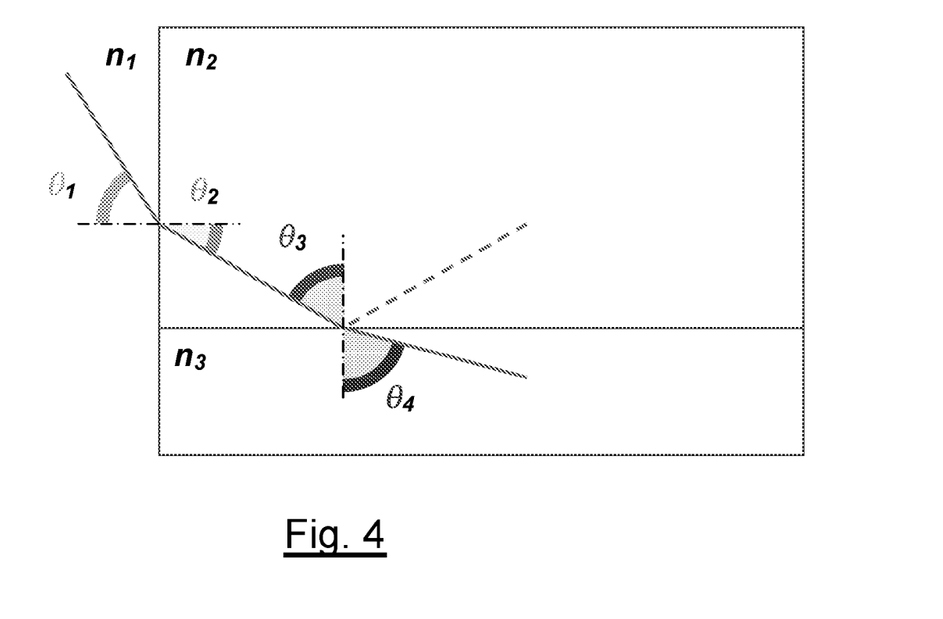
FIG. 4 is a simplified diagram of refraction of the light outside the moisture sensor in case it is at contact with means having a sufficiently high refractive index $n_3$.

With particular reference to FIGS. 3 and 4, l corresponds the thickness of the plate-sensor 1 and $\theta_1$ to the angle of incidence of the light radiation, in absence of contact with the skin, $n_1$ and $n_2$ being the refractive indices respectively of air ($n_1=1$) and glass ($n_2=1.5$), according to Snell's law the light remains trapped in the plate-sensor 1 until it laterally projects therefrom without emitting light from the upper and lower surface (see FIG. 3). In this case, the reflective angle $\theta_3=\theta_4$ is given by:

$$\theta_3 = 90° - \arcsin\left(\frac{n_1}{n_2}\sin\theta_1\right)$$

FIG. 3 (the dimensions are not in scale, the height being much smaller than the length and the width of the sensor) shows a side view of the diagram for the total reflection of light within the moisture sensor 1.

Instead, in cases where the surface of the sensor does not have air, but something with sufficiently high refractive index $n_3$ (for example water, refractive index 1.333), the light may not remain trapped by the plate-sensor, but by some values of the angle $\theta_1$ it partly exits from the surface, as shown in FIG. 4, with an angle $\theta_4$ given by:

$$\theta_4 = \arcsin\left(\frac{n_2}{n_3}\sin\theta_3\right)$$

Figure 5:
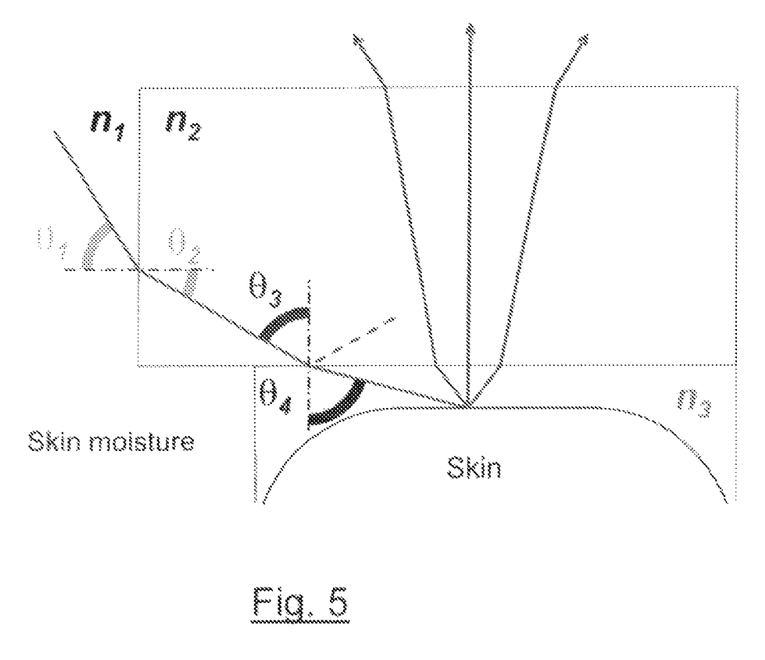
FIG. 5 is a simplified diagram of the refraction/diffusion of the light through the moisture sensor due to the contact with the moist skin.

In the case where the skin (moist skin and thus containing water) is at contact with the sensor there occurs the previously described situation, and thus the light spreads and it is reflected by the skin, up to exiting from the opposite side of the sensor, as shown in FIG. 5. By adjusting the light intensity (so that it is sufficient to overcome the environmental lighting) and the angle of incidence $\theta_1$ the image of the part of the skin actually at contact with the surface of the sensor can be displayed in a detailed manner. The angle of incidence $\theta_1$ shall be comprised between a minimum of 45° and a maximum of 80° (calculated considering the refractive index of glass and water respectively 1.5 and 1.333).

Figure 6:
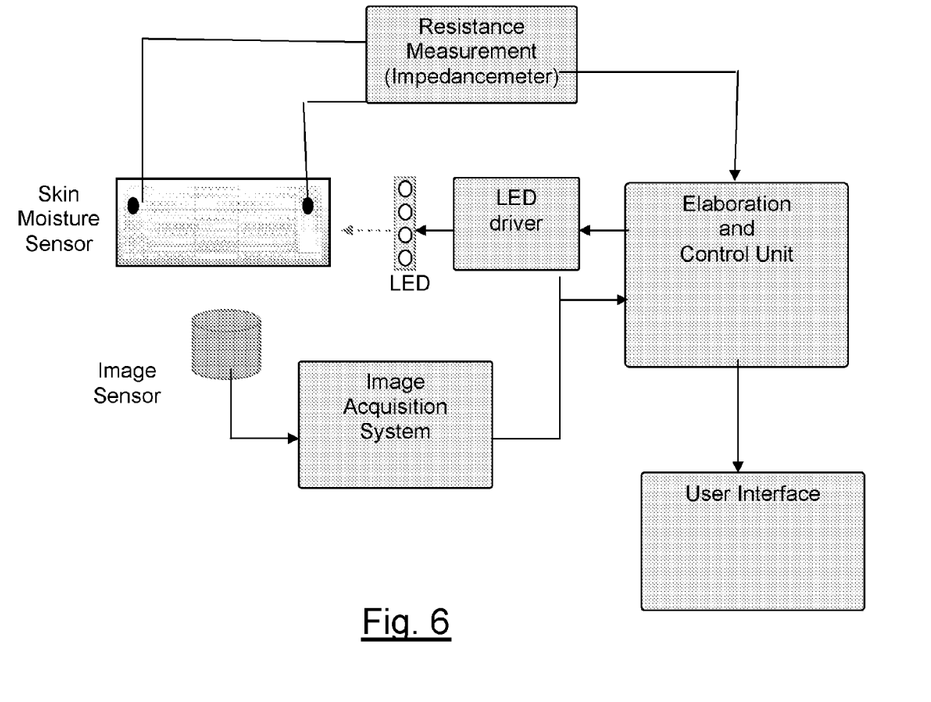
FIG. 6 shows a functional block diagram of the device according to the invention.

From an architectural point of view the complete measurement system can be schematized as shown in FIG. 6. The skin moisture resistive sensor is connected to a module for measuring resistance thereof (an impedance meter or an equivalent electronic measurement circuit), which transmits the measurement carried out to a processing and control unit. Such processing and control unit also manages the user interface, the driver for the source of lighting as well as the processing of the images sampled by the image sensor through the acquisition module with resolution sufficient to capture the detail of the image. The processing and control unit includes a software which processes the resistance measurements carried out and the sampled images so as to obtain the normalized skin moisture measurement as the final result, according to the diagram shown in FIG. 7.

Figure 7:
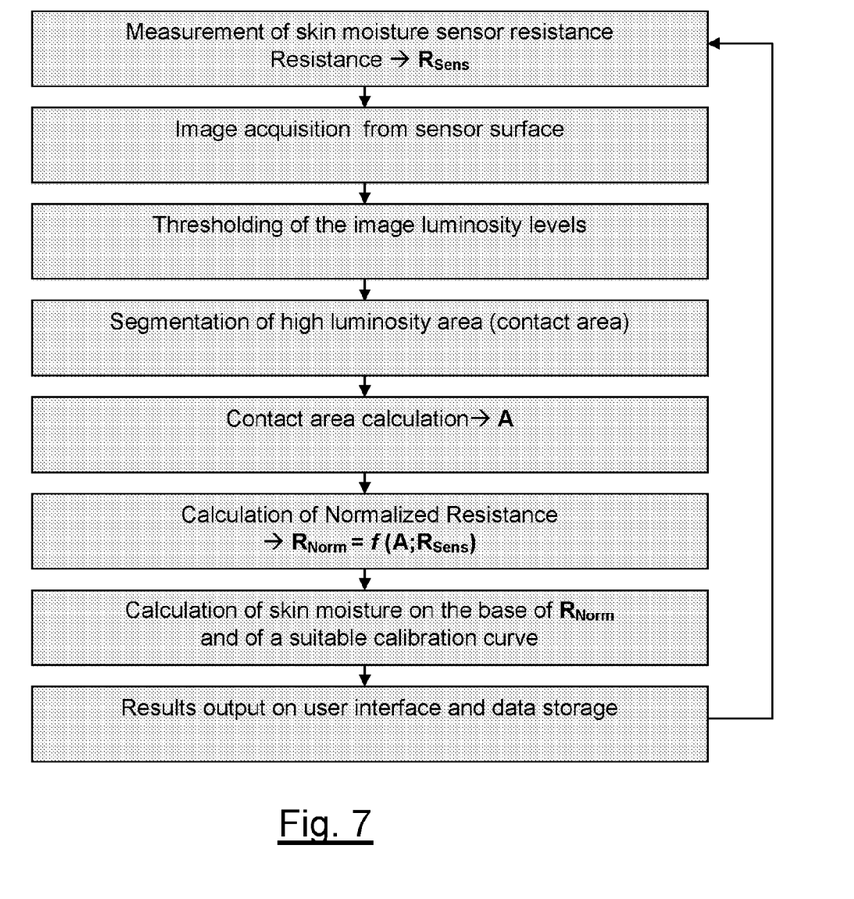
FIG. 7 is a block diagram of the operative sequence of the skin moisture measurement device according to the invention.

In particular the sampled image is subjected to thresholding and segmentation to highlight the pixels with lighting greater than a given threshold (which correspond to support points of the skin on the sensor). Hence, the area of contact is obtained from the image thus segmented by multiplying the area of each pixel (known from the geometric and construction parameters of the system) by the number of pixels. The executed measurement of the resistance of the sensor is thus normalised through a suitable algorithm to obtain a normalized resistance value. In particular, given the resistance measurement in ohms, the normalised measurement is defined in this specific case as the ratio between the resistance and the reverse of the contact area by a constant. Lastly, calibration curves or tables (determined according to the reference measurements carried out using systems deemed standard such as the Dermovisuals Corneometer) are used for obtaining the value of the skin moisture, which is displayed through the user interface.

From what has been described above, it is clear that the invention allows attaining the aimed objects. In particular, the system according to the invention allows accurately measuring the degree of skin moisture and simultaneously the actual contact surface to have a normalized measurement. The system also allows visually accessing the contact surface to obtain visual/morphological data therefrom. Thus, the measurement system according to the invention allows studying the physical and mechanical aspects related to the tactile perception in that it allows addressing the study of the influence of the degree of skin moisture on the biomechanical dynamic behaviour.

The system for detecting and measuring the degree of human skin moisture according to the present invention may be subjected to variants and modifications without departing from the scope of the invention as defined in the following claims.

The invention claimed is:

1. A human skin moisture measuring device comprising:
  a transparent interdigitated resistive sensor configured to contact the skin;
  a plate-like transparent support comprising a first face in contact with the transparent interdigitated resistive sensor;
  image sensing means turned towards a second face that is opposite said first face of said support;
  a lighting device configured to direct light radiation within said support at a prefixed angle; and
  means for processing a first signal from said transparent interdigitated resistive sensor and a second signal from said image sensing means,
  wherein said processing includes calculating a contact area between the skin and the sensor based on said second signal, normalizing said first signal based on said contact area, and outputting a value of moisture degree based on the normalized first signal.

2. The device according to claim 1, wherein
  said plate-like transparent support is a flat plate defined by a side flank or thickness and
  said lighting device is arranged substantially coplanar relative to said flat plate, whereby the plate is irradiated through its thickness.

3. The device according to claim 2, wherein an incidence angle ($\theta_1$) of the light radiation emitted by said lighting device is comprised between 45° and 80°.

4. The device according to claim 1, wherein said lighting device is formed by one or more lighting sources of LED type.

5. The device according to claim 1, wherein said image sensing means comprise a video camera, a CCD device or a CMOS device.

6. A human skin moisture measurement method comprising:
  measuring skin resistance by a transparent interdigitated resistive sensor;
  acquiring an image of a skin portion contacting a sensor surface through said sensor;
  calculating, using a processing unit, a contact area between the skin portion and the sensor based on said image;
  normalizing, using the processing unit, said skin resistance based on said contact area; and
  determining, using the processing unit, skin moisture as a function of said normalized resistance.

7. The method according to claim 6, wherein said acquiring the image is obtained by lighting the skin surface contacting the surface of the sensor by a light beam directed against a side of said sensor and inclined of an angle of at least 45° with respect to a perpendicular line thereof.

8. The method according to claim 7, wherein the incidence angle of the light beam is comprised between 45° and 80°.

9. The method according to claim 6, further comprising performing thresholding of the luminosity levels of the image of the skin portion in contact with the sensor surface and segmentation of the highest luminosity area to determine the measure of the skin-sensor contact surface area.

10. The method according to claim 6, wherein the skin moisture as a function of the normalized resistance measure is determined through calibration curves or tables.

* * * * *